US011676603B2

(12) United States Patent
Erramilli et al.

(10) Patent No.: US 11,676,603 B2
(45) Date of Patent: Jun. 13, 2023

(54) CONVERSATIONAL AGENT FOR HEALTHCARE CONTENT

(71) Applicant: ACTO Technologies Inc., Toronto (CA)

(72) Inventors: Kumar Karthik Erramilli, Scarborough (CA); Parth Khanna, Toronto (CA); Kapil Kalra, Mississauga (CA)

(73) Assignee: ACTO Technologies Inc., Toronto (CA)

( * ) Notice: Subject to any disclaimer, the term of this patent is extended or adjusted under 35 U.S.C. 154(b) by 41 days.

(21) Appl. No.: 16/888,244

(22) Filed: May 29, 2020

(65) Prior Publication Data
US 2020/0379986 A1 Dec. 3, 2020

Related U.S. Application Data

(60) Provisional application No. 62/855,224, filed on May 31, 2019.

(51) Int. Cl.
*G10L 15/26* (2006.01)
*G16H 70/40* (2018.01)

(52) U.S. Cl.
CPC ............ *G10L 15/26* (2013.01); *G16H 70/40* (2018.01)

(58) Field of Classification Search
CPC ............ G06F 16/243; G06F 16/24522; G06F 16/90332; G06F 40/30; G10L 15/26; G16H 70/40; G16H 80/00; G06N 5/04
See application file for complete search history.

(56) References Cited

U.S. PATENT DOCUMENTS

| 11,048,870 | B2 * | 6/2021 | Bakis | G06F 40/10 |
| 11,062,704 | B1 * | 7/2021 | Kodish-Wachs | G06F 40/30 |
| 2002/0042725 | A1 * | 4/2002 | Mayaud | G16H 70/40 |
| | | | | 705/2 |
| 2013/0339030 | A1 * | 12/2013 | Ehsani | G10L 17/00 |
| | | | | 704/275 |
| 2015/0150098 | A1 * | 5/2015 | Murphy | G16H 10/60 |
| | | | | 726/4 |
| 2015/0187228 | A1 * | 7/2015 | Boguski | G16H 20/10 |
| | | | | 434/262 |
| 2016/0012194 | A1 * | 1/2016 | Prakash | G16H 40/40 |
| | | | | 705/2 |

(Continued)

*Primary Examiner* — Fariba Sirjani
(74) *Attorney, Agent, or Firm* — Fernando & Partners, LLP

(57) ABSTRACT

Various implementations disclosed herein include devices, systems, and methods for indicating whether a conversation regarding a subject satisfies a boundary condition associated with the subject. In various implementations, a device includes a display, a processor and a non-transitory memory. In some implementations, the method includes detecting a conversation in which a person is conveying information regarding a subject. In some implementations, the method includes determining whether the information satisfies a boundary condition associated with the subject. In some implementations, the boundary condition is defined by a set of one or more content items related to the subject. In some implementations, the method includes displaying an indicator that indicates whether or not the information being conveyed by the person satisfies the boundary condition associated with the subject.

18 Claims, 11 Drawing Sheets

(56) References Cited

U.S. PATENT DOCUMENTS

| | | | |
|---|---|---|---|
| 2016/0048655 A1* | 2/2016 | Maitra | G16H 70/40 |
| | | | 705/3 |
| 2019/0065464 A1* | 2/2019 | Finley | G06F 40/169 |
| 2019/0147992 A1* | 5/2019 | Hill, Sr. | G16H 15/00 |
| | | | 705/3 |
| 2019/0206553 A1* | 7/2019 | Are | G16H 10/60 |
| 2020/0342999 A1* | 10/2020 | Rubin | G06Q 50/26 |
| 2020/0379986 A1* | 12/2020 | Erramilli | G10L 15/26 |
| 2021/0210213 A1* | 7/2021 | Dai | G16H 50/70 |

* cited by examiner

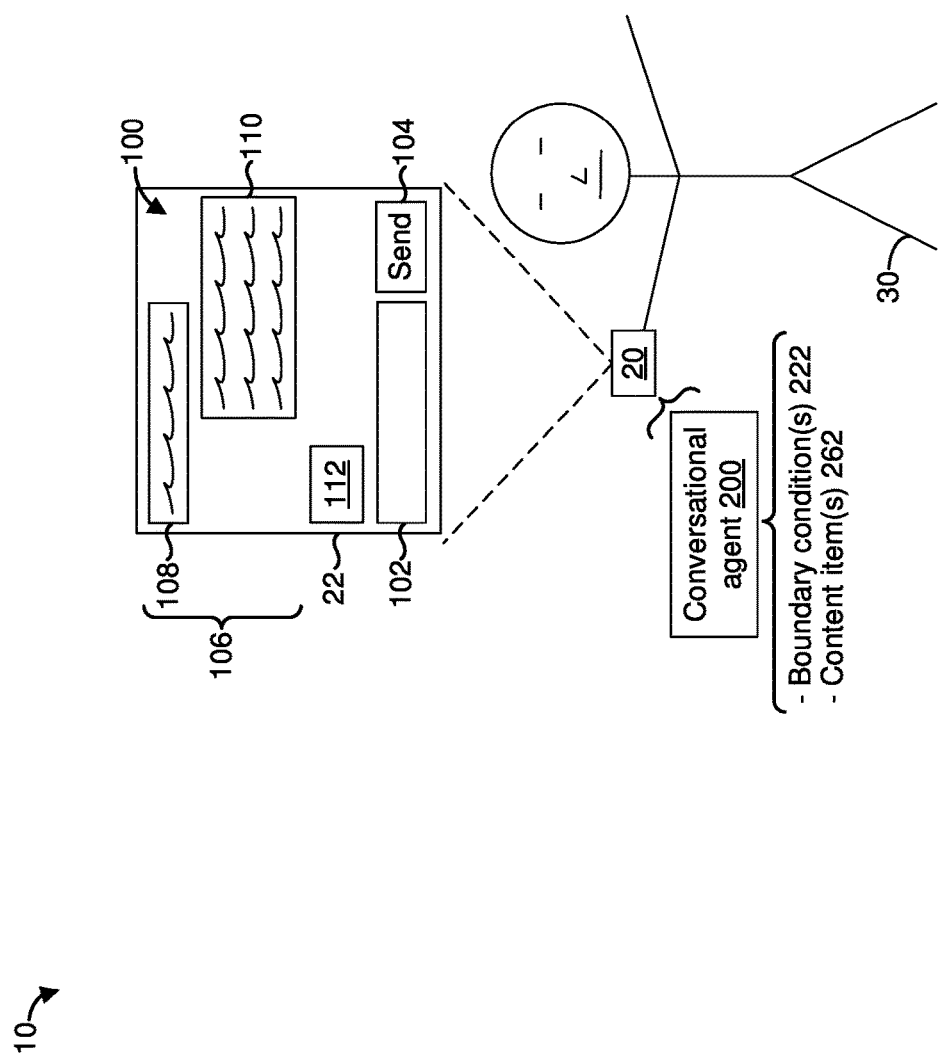

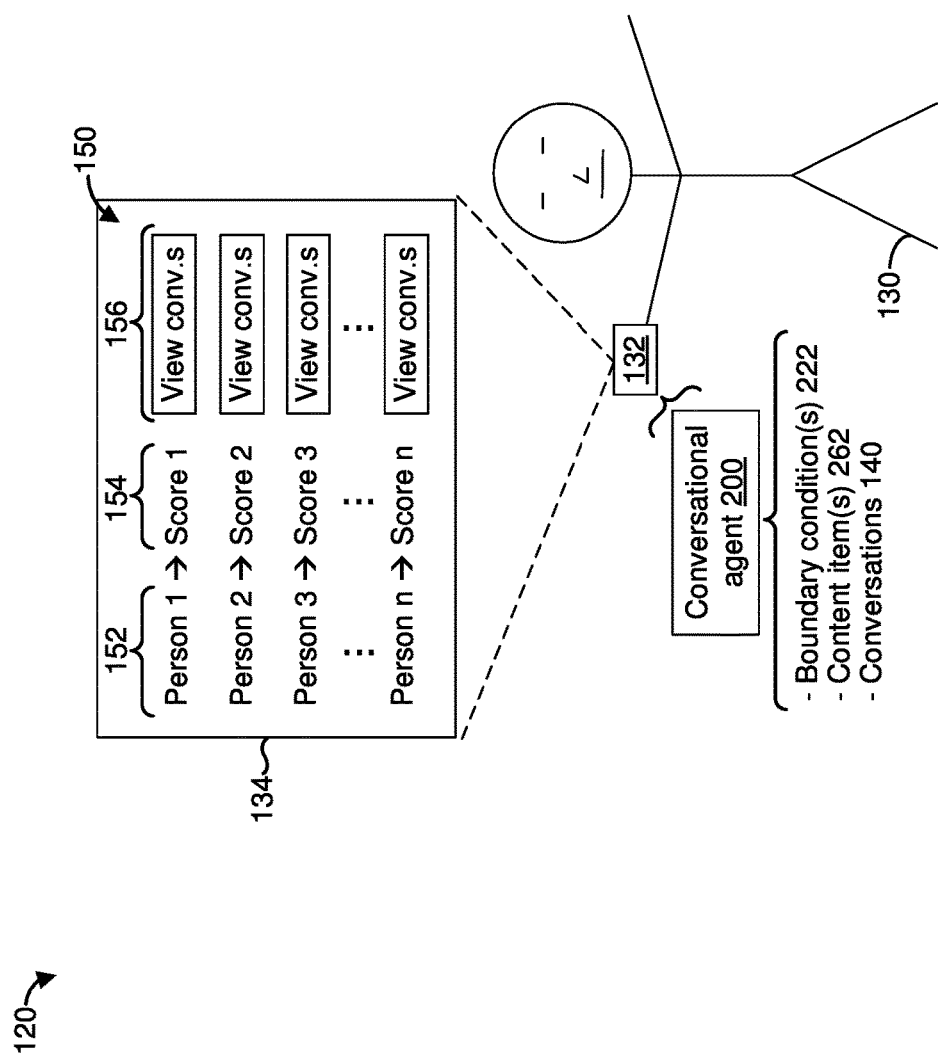

CONVERSATIONAL AGENT FOR HEALTHCARE CONTENT

CROSS-REFERENCE TO RELATED APPLICATION

This application claims the benefit of U.S. Provisional Patent App. No. 62/855,224, filed on May 31, 2019, which is incorporated by reference in its entirety.

TECHNICAL FIELD

The present disclosure generally relates to a conversational agent for healthcare content.

BACKGROUND

Some devices allow a user to view information regarding a subject. For example, some devices allow a user to search or scroll through a document in order to locate specific information regarding the subject. Searching or scrolling through a document can sometimes be resource-intensive and time-consuming. Searching or scrolling through a document tends to drain a battery of a battery-operated device. Searching for information regarding the subject during a conversation can be distracting and result in the conversation being interrupted.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

FIGS. 1A-1G are diagrams of an example operating environment in accordance with some implementations.

Figure 1A:
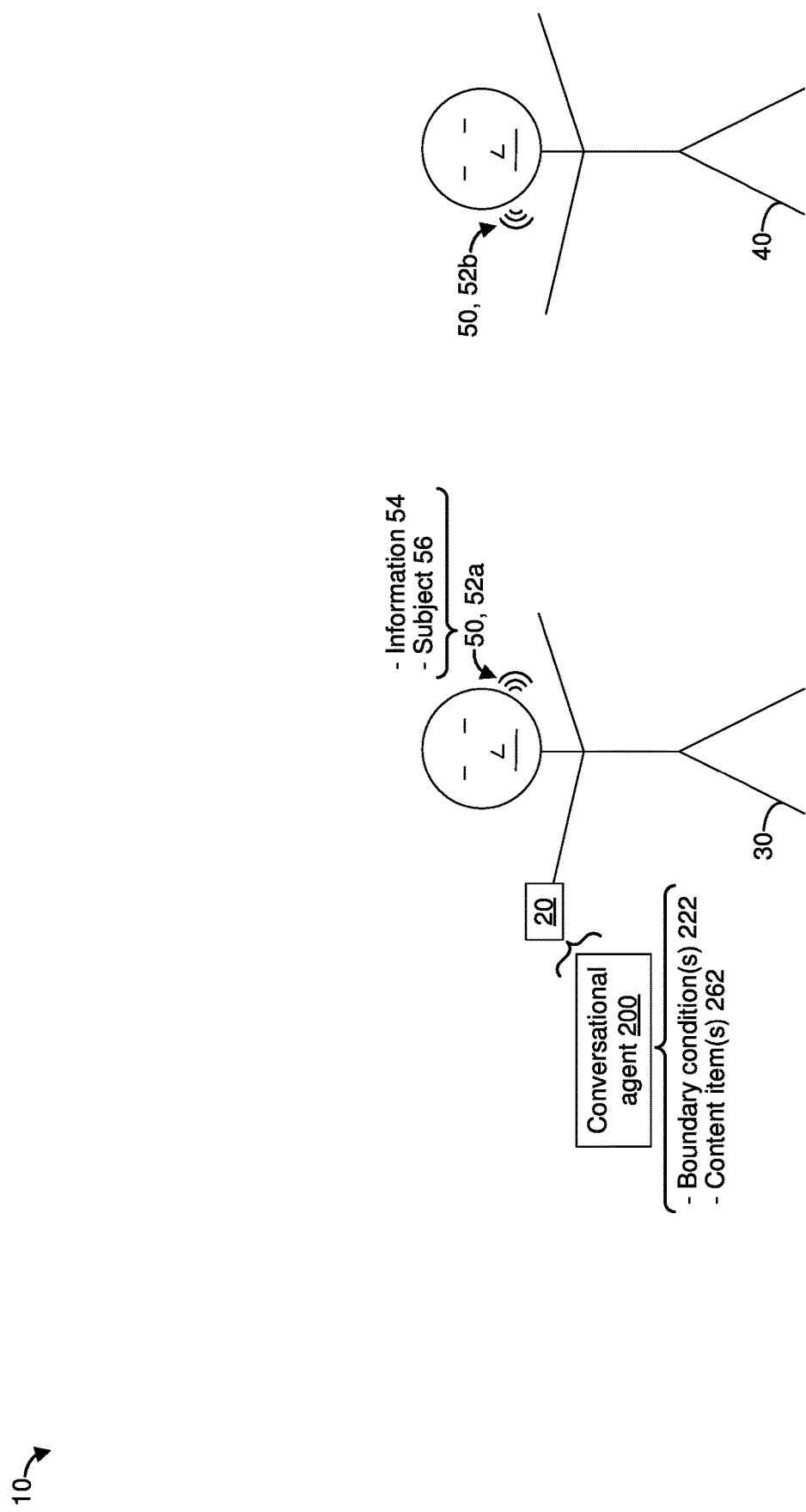

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

SUMMARY

Various implementations disclosed herein include devices, systems, and methods for indicating whether a conversation regarding a subject satisfies a boundary condition associated with the subject. In various implementations, a device includes a display, a processor and a non-transitory memory. In some implementations, the method includes detecting a conversation in which a person is conveying information regarding a subject. In some implementations, the method includes determining whether the information satisfies a boundary condition associated with the subject. In some implementations, the boundary condition is defined by a set of one or more content items related to the subject. In some implementations, the method includes displaying an indicator that indicates whether or not the information being conveyed by the person satisfies the boundary condition associated with the subject.

In accordance with some implementations, a device includes one or more processors, a non-transitory memory, and one or more programs. In some implementations, the one or more programs are stored in the non-transitory memory and are executed by the one or more processors. In some implementations, the one or more programs include instructions for performing or causing performance of any of the methods described herein. In accordance with some implementations, a non-transitory computer readable storage medium has stored therein instructions that, when executed by one or more processors of a device, cause the device to perform or cause performance of any of the methods described herein. In accordance with some implementations, a device includes one or more processors, a non-transitory memory, and means for performing or causing performance of any of the methods described herein.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects and/or variants do not include all of the specific details described herein. Moreover, well-known systems, methods, components, devices, and circuits have not been described in exhaustive detail so as not to obscure more pertinent aspects of the example implementations described herein.

It is resource-intensive to determine whether information being conveyed in a conversation regarding a subject is accurate. For example, it is resource-intensive to determine whether information being conveyed in a conversation regarding a pharmaceutical drug or a medical device is consistent with information that has been approved by the Food and Drug Administration (FDA). Searching or scrolling through FDA-approved documents to determine whether information being conveyed in a conversation is accurate detracts from a user experience. Moreover, requiring unnecessary user inputs that correspond to searching or scrolling through source material tends to drain a battery of a battery-operated device thereby adversely impacting operability of the device.

The present disclosure provides methods, systems, and/or devices for displaying an indicator that indicates whether information being conveyed regarding a subject is consistent with information provided by source material related to the subject. The device displays an indicator that indicates whether conversational information being conveyed regarding a subject matches information provided by a source material regarding the subject. For example, the indicator indicates whether information being conveyed in a conversation regarding a particular pharmaceutical drug or a medical device is consistent with information included in an FDA-approved label for that particular pharmaceutical drug or medical device.

Displaying the indicator reduces the need to search or scroll through source material in order to determine the accuracy of the information that is being conveyed. Automatically displaying the indicator reduces unnecessary user inputs that correspond to searching or scrolling through source material such as an FDA-approved label for a pharmaceutical drug or a medical device. Reducing unnecessary user inputs tends to enhance a user experience of the device. Reducing unnecessary user inputs tends to improve a battery-life of a battery-operated device thereby improving operability of the device.

FIG. 1A is a diagram of an example operating environment 10 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating environment 10 includes an electronic device 20, a first person 30 that is a user of the electronic device 20 and a second person 40. In some implementations, the electronic device 20 includes a handheld computing device that can be held by the first person 30. For example, in some implementations, the electronic device 20 includes a smartphone, a tablet, a media player, a laptop, or the like. In some implementations, the electronic device 20 includes a wearable computing device that can be worn by the first person 30. For example, in some implementations, the electronic device 20 includes an electronic watch, a pair of headphones or a head-mountable device.

In various implementations, the electronic device 20 detects that the first person 30 is engaged in a conversation 50 with the second person 40. In some implementations, the electronic device 20 detects that the first person 30 is engaged in the conversation 50 by detecting a first utterance 52a by the first person 30 and/or a second utterance 52b by the second person 40. In some implementations, the electronic device 20 detects the first utterance 52a and/or the second utterance 52b via an audio sensor (e.g., a microphone). In the example of FIG. 1A, the conversation 50 is an in-person conversation because the first person 30 and the second person 40 are collocated in the operating environment 10.

In some implementations, the conversation 50 includes information 54 regarding a subject 56. In some implementations, the first person 30 is conveying the information 54 regarding the subject 56. Alternatively, in some implementations, the second person 40 is conveying the information 54 regarding the subject 56. In some implementations, the subject 56 of the conversation 50 is a pharmaceutical drug, and the information 54 includes pharmacological information regarding the pharmaceutical drug. For example, in some implementations, the information 54 includes dosage information for the pharmaceutical drug. In some implementations, the information 54 includes prescriptible uses for the pharmaceutical drug. In some implementations, the information 54 includes side effects of the pharmaceutical drug.

In some implementations, the subject 56 of the conversation 50 is a medical device, and the information 54 includes pharmacological information regarding the medical device. For example, in some implementations, the information 54 includes medical conditions under which the medical device can be used. In some implementations, the information 54 includes instructions to use the medical device. In some implementations, the information 54 includes side effects of using the medical device. In some implementations, the information 54 includes medical conditions under which the medical device can be prescribed.

In some implementations, the subject 56 of the conversation 50 is a medical condition, and the information 54 includes a treatment plan for the medical condition. For example, in some implementations, the information 54 includes a recommendation to administer a pharmaceutical drug in order to treat the medical condition. In some implementations, the information 54 includes a recommendation to utilize a medical device in order to treat the medical condition. In some implementations, the information 54 includes a recommendation to administer a pharmaceutical drug in combination with using a medical device to treat the medical condition.

In various implementations, the electronic device 20 includes (e.g., implements) a conversational agent 200. In the example of FIG. 1A, the conversational agent 200 monitors the conversation 50 and determines whether the information 54 regarding the subject 56 satisfies one or more boundary conditions 222 associated with the subject 56. In some implementations, the conversational agent 200 extracts the boundary condition(s) 222 from one or more content items 262 that provide information regarding the subject 56.

Figure 1B:
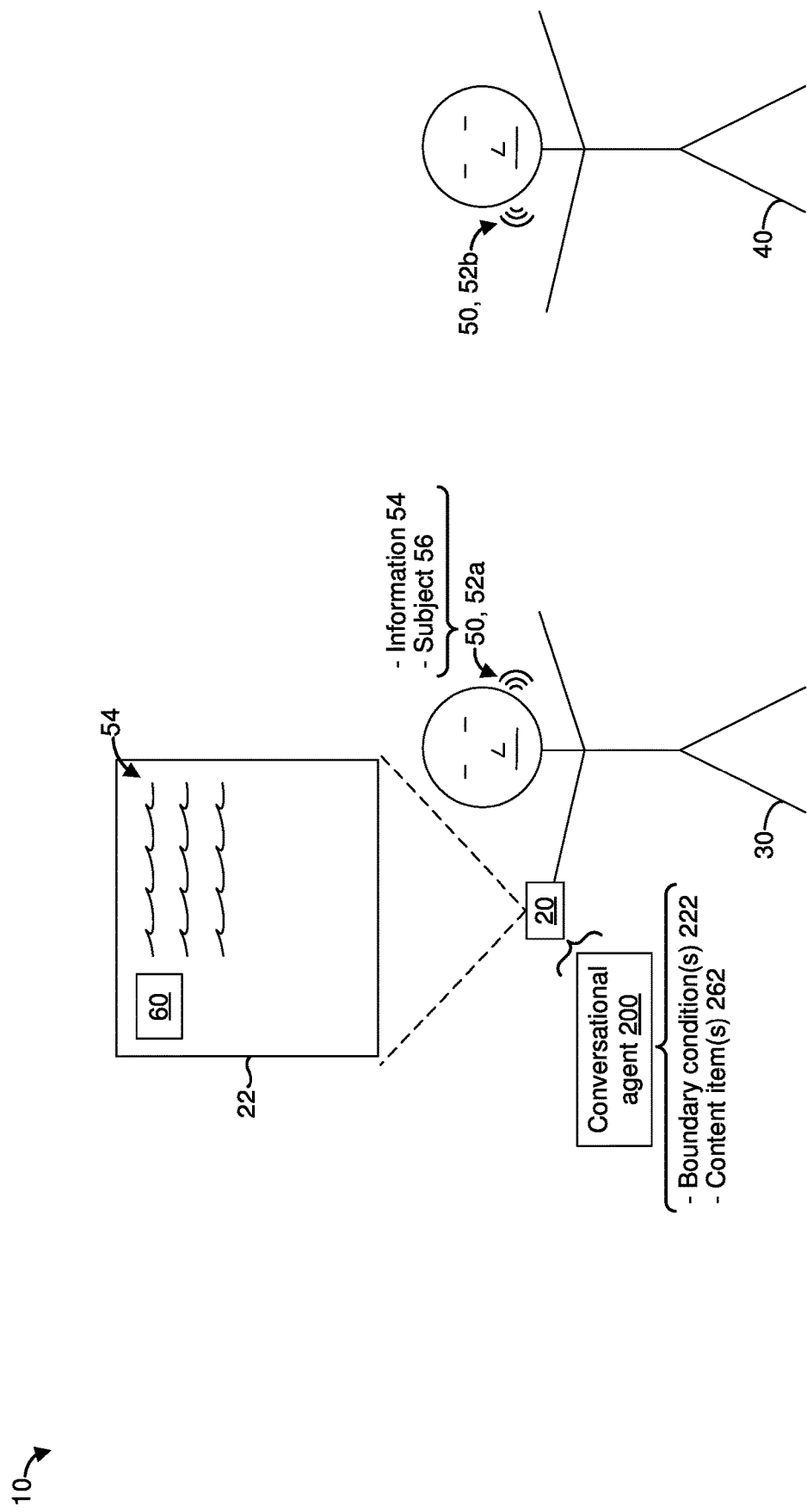

Referring to FIG. 1B, in some implementations, the electronic device 20 (e.g., the conversational agent 200) displays an indicator 60, on a display 22 of the electronic device 20, indicating whether or not the information 54 being conveyed in the conversation 50 satisfies the boundary conditions(s) 222. In some implementations, the electronic device 20 displays the indicator 60 in association with the information 54. In the example of FIG. 1B, the electronic device 20 displays the indicator 60 adjacent to the information 54. Displaying the indicator 60 reduces the need for the first person 30 to search the content item(s) 262 in order to determine whether the information 54 being conveyed in the conversation 50 satisfies the boundary condition(s) 222 associated with the subject 56. Displaying the indicator 60 provides the first person 30 an opportunity to correct the information 54 so that the information 54 satisfies the boundary condition(s) 222 associated with the subject 56.

Figure 1C:
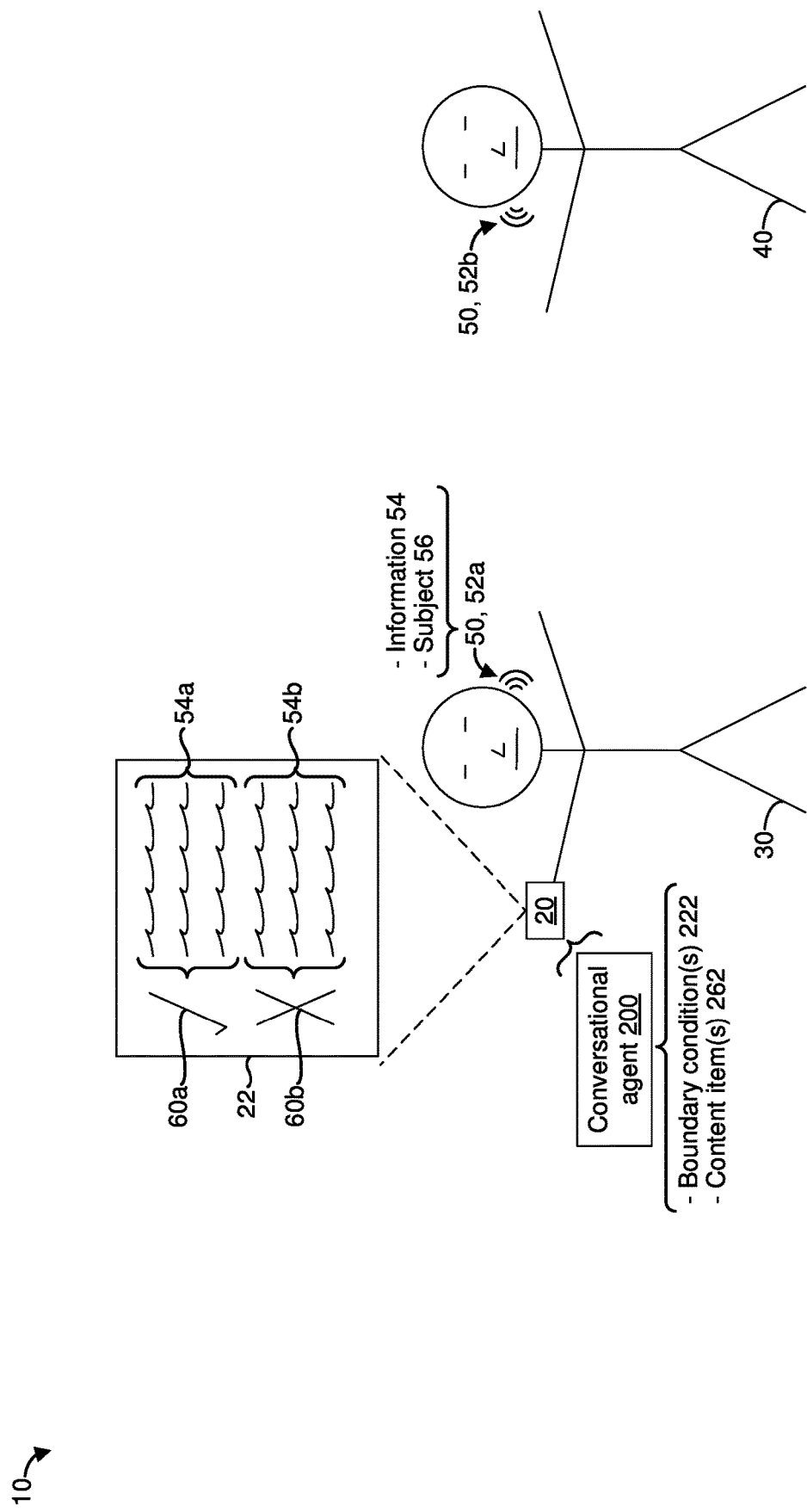

Referring to FIG. 1C, in some implementations, the electronic device 20 (e.g., the conversational agent 200) displays a satisfaction indicator such as a checkmark 60a in association with (e.g., adjacent to) a first portion Ma of the information 54 in order to indicate that the first portion 54a of the information 54 satisfies the boundary condition(s) 222 associated with the subject 56. In some implementations, the electronic device 20 displays a breach indicator such as a cross 60b in association with (e.g., adjacent to) a second portion 54b of the information 54 in order to indicate that the second portion 54b of the information 54 breaches (e.g., does not satisfy) the boundary condition(s) 222 associated with the subject 56. Indicating which portions of the information 54 satisfy the boundary condition(s) 222 and which portions of the information 54 breach the boundary condition(s) 222 provides the first person 30 an opportunity to correct the portions of the information 54 that breach the boundary condition(s) 222 while not having to correct the portions of the information 54 that satisfy the boundary condition(s) 222.

Figure 1D:
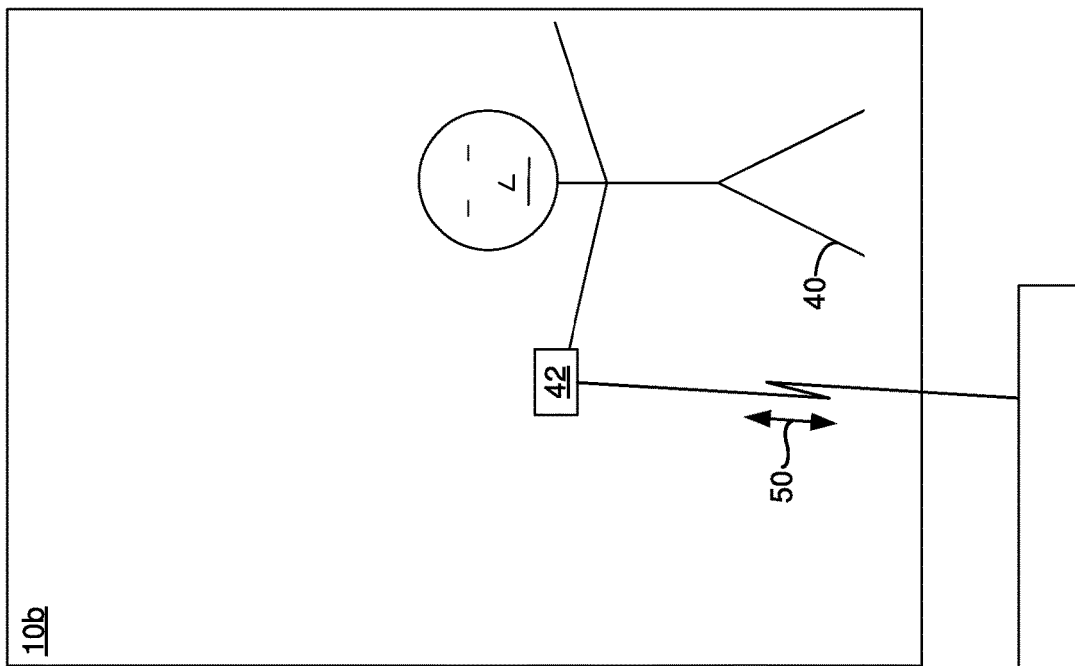
Figure 1D:
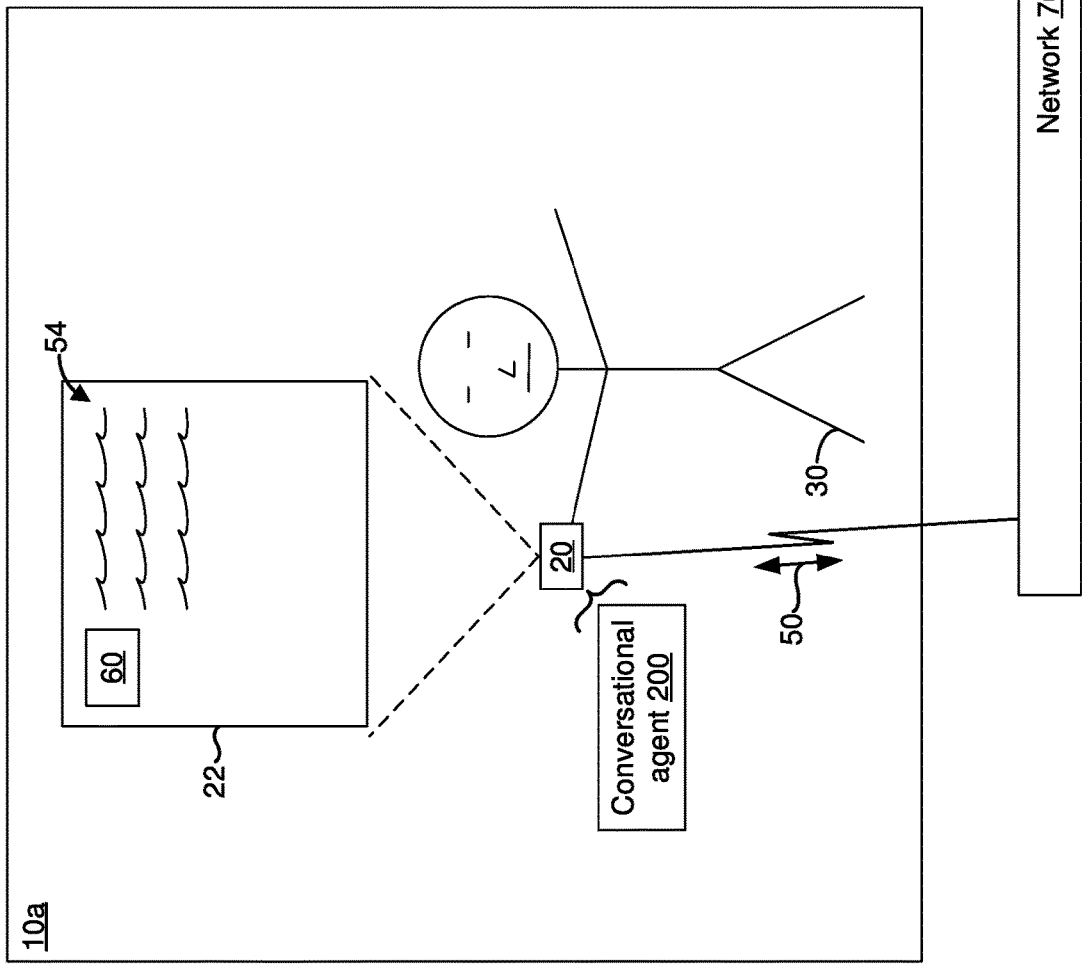

Referring to FIG. 1D, in some implementations, the first person 30 and the electronic device 20 are located in a first physical environment 10a, and the second person 40 is located in a second physical environment 10b that is different from the first physical environment 10a. In the example of FIG. 1D, the second person 40 is using an electronic device 42 (e.g., a smartphone, a tablet, a laptop computer or a desktop computer).

In the example of FIG. 1D, the conversation 50 is a virtual conversation that takes place via a network 70 (e.g., a portion of the Internet). For example, in some implementations, the conversation 50 is a voice conversation (e.g., a phone call or a voice chat). In some implementations, the conversation 50 is a video conversation (e.g., a teleconference or a video chat). In some implementations, the conversation 50 is a messaging conversation that takes place via an instant messaging application, a social networking application or short message service (SMS). In some implementations, the conversation 50 occurs via an application such as a teleconferencing application, a messaging application, a social networking application, an email application, etc.

Figure 1E:
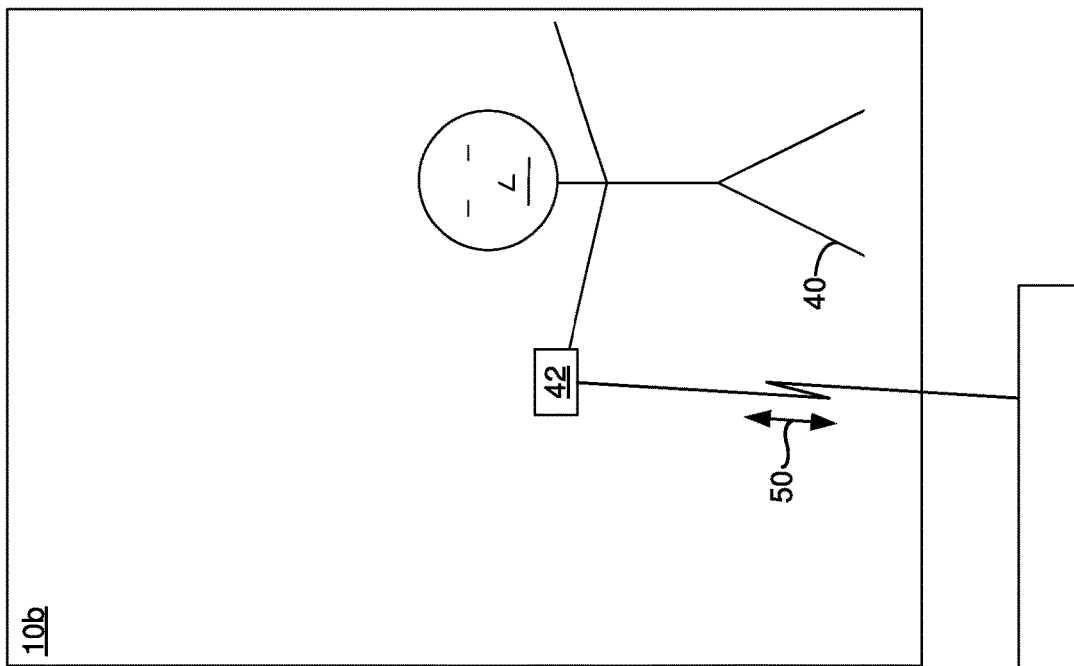
Figure 1E:
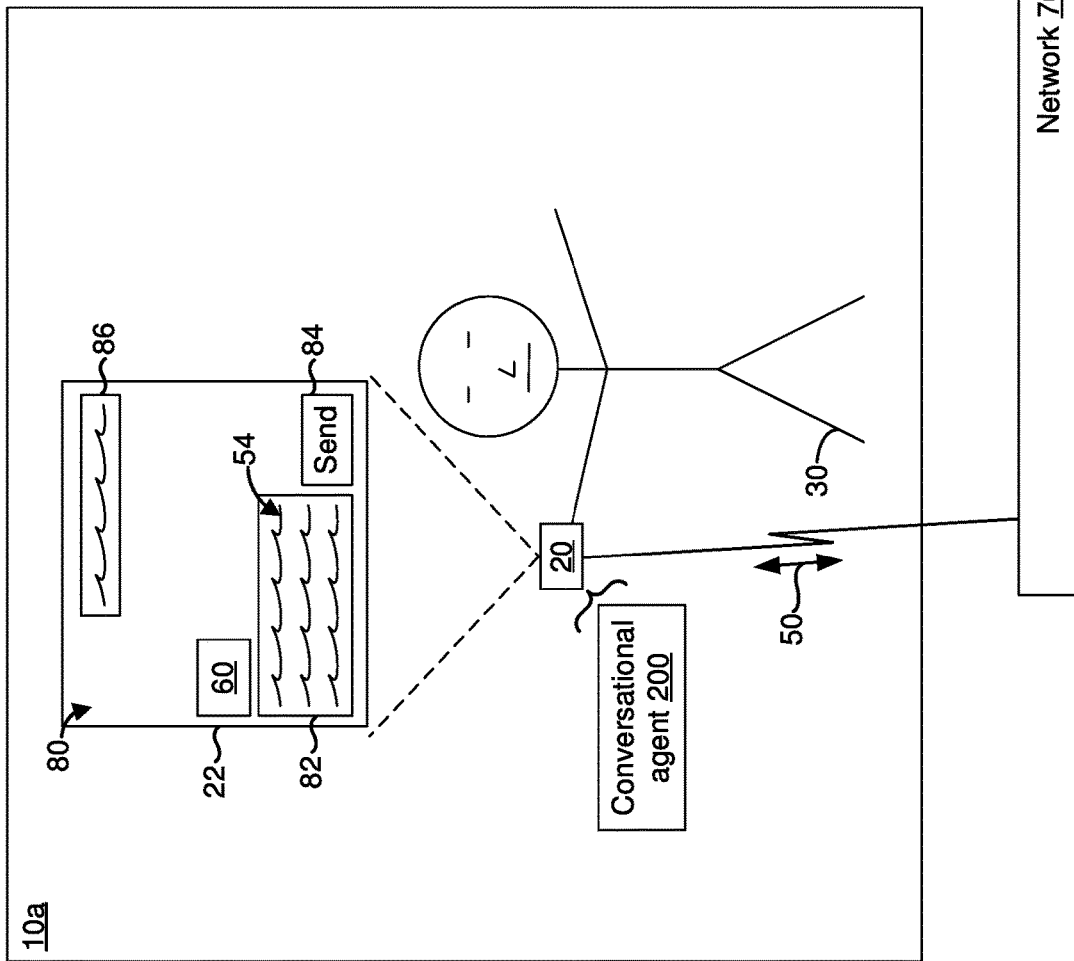

Referring to FIG. 1E, in some implementations, the electronic device 20 displays a messaging graphical user interface (GUI) 80. In some implementations, the messaging GUI 80 includes a message composition region 82 for composing a message, a send affordance 84 (e.g., a send button) and one or more previous messages 86 that have been sent or received by the electronic device 20. In the example of FIG. 1E, the message composition region 82 displays the information 54. The electronic device 20 is configured to transmit the information 54 to the electronic device 42 when the first person 30 activates (e.g., selects) the send affordance 84. As such, in the example of FIG. 1E, the first person 30 has not yet conveyed the information 54 to the second person 40. However, the first person 30 is in the process of conveying the information 54 to the second person 40.

In some implementations, the electronic device 20 (e.g., the conversational agent 200) displays the indicator 60 in association with the message composition region 82 in order to indicate whether or not the information 54 in the message composition region 82 satisfies the boundary condition(s) 222 associated with the subject 56. As such, the indicator 60 provides the first person 30 with an option to modify the information 54 in order to satisfy the boundary condition(s) 222 before the information 54 is conveyed to the second person 40. Providing the first person 30 with the option to modify the information 54 before conveying the information 54 to the second person 40 reduces the need to correct the information 54 after the information 54 has been conveyed to the second person 40.

In the examples of FIGS. 1A-1E, in some implementations, the first person 30 is a medical representative, and the second person 30 is a healthcare provider (e.g., a physician, a physician's assistant, a nurse practitioner, a nurse, etc.). In such implementations, the electronic device 20 monitors the conversation 50 between the medical representative and the healthcare provider after receiving consent from the healthcare provider. In some implementations, the first person 30 is a healthcare provider and the second person 40 is a patient. In such implementations, the electronic device 20 monitors the conversation 50 between the healthcare provider and the patient after receiving consent from the patient. More generally, in various implementations, the electronic device 20 monitors the conversation 50 after receiving consent from the first person 30 and/or the second person 40.

FIG. 1F illustrates an example chatbot interface 100 that includes a message composition region 102 for composing a message and a submit affordance 104. In some implementations, the conversational agent 200 includes (e.g., implements) a chatbot that converses with the first person 30. In the example of FIG. 1F, the first person 30 and the conversational agent 200 are engaged in a conversation 106. In some implementations, the conversation 106 includes a machine-generated message 108 that was generated by the conversational agent 200, and a human-curated response 110 that was curated by the first person 30. In some implementations, the machine-generated message 108 includes a query (e.g., a question) regarding the subject 56, and the human-curated response 110 includes a response to the query (e.g., an answer to the question).

In some implementations, the conversation agent 200 determines whether the human-curated response 110 satisfies the boundary condition(s) 222 associated with the subject 56, and displays an indicator 112 indicating whether or not the human-curated response 110 satisfies the boundary condition(s) 222 associated with the subject 56. In some implementations, the machine-generated message 108 is a question, the human-curated response 110 is an answer to the question, and the indicator 112 indicates whether or not the answer provided by the first person 30 is correct. In various implementations, the conversational agent 200 allows the first person 30 to learn information regarding the subject 56 by asking questions to the conversation agent 200 and/or by answering questions generated by the conversational agent 200.

FIG. 1G illustrates an example operating environment 120 that includes an operator 130 (e.g., an administrator) and an electronic device 132 (e.g., an administrator device). In some implementations, the electronic device 132 displays a GUI 150 on a display 134 of the electronic device 132. In some implementations, the GUI 150 displays person identifiers 152 that identify respective persons. For example, one of the person identifiers 152 identifies the first person 30 shown in FIGS. 1A-1F. In some implementations, the person identifier 152 includes names, user identifiers (IDs), etc.

In some implementations, the GUI 150 displays respective scores 154 for the persons associated with the person identifiers 152. In some implementations, the scores 154 indicate how often the persons breach or satisfy the boundary condition(s) 222 associated with the subject 56. In some implementations, the conversational agent 200 determines the scores 154 based on conversations 140 of the persons. In some implementations, the conversations 140 includes previous conversations (e.g., past conversations that have been recorded and/or transcribed with the persons' consent). In some implementations, the conversations 140 include current conversations (e.g., ongoing conversations). In various implementations, the conversational agent 200 determines the scores 154 by determining whether information conveyed in the conversations 140 breaches the boundary condition(s) 222.

In some implementations, the scores 154 includes numerical values. For example, in some implementations, the scores 154 range from a first numerical value (e.g., 0) to a second numerical value (e.g., 100). In some implementations, a score 154 within a threshold of the first numerical value (e.g., scores 154 closer to 0) indicates that conversations 140 of the corresponding person breach the boundary condition(s) 222 more than a threshold number of times (e.g., a score 154 of 0 indicates that all conversations 140 of the person breach the boundary condition(s) 222, a score 154 of 10 indicates that 10% of the conversations 140 of the person satisfy the boundary condition(s) 222). In some implementations, a score 154 within a threshold of the second numerical value (e.g., scores 154 closer to 100) indicates that conversations 140 of the corresponding person satisfy the boundary condition(s) 222 more than a threshold number of times (e.g., a score 154 of 100 indicates that all conversations 140 of the person satisfy the boundary condition(s) 222, a score 154 of 95 indicates that 95% of the conversations 140 of the person satisfy the boundary condition(s) 222, etc.). In some implementations, the scores 154 include letter grades (e.g., A+, A, A−, . . . , and F).

In some implementations, the GUI 150 includes view affordances 156 that allow the operator 130 to view at least some of the conversations 140 that the conversational agent 200 utilized in determining the scores 154. In some implementations, the electronic device 20 detects a selection of a particular view affordance 156 (e.g., the view affordance 156 for Person 1). In such implementations, the electronic device 20 displays the conversations 140 of Person 1 (e.g., all conversations 140 of Person 1). In some implementations, the electronic device 20 displays portions of the conversations 140 that breached the boundary condition(s) 222, and forgoes displaying portions of the conversations 140 that satisfy the boundary condition(s) 222.

Figure 2A:
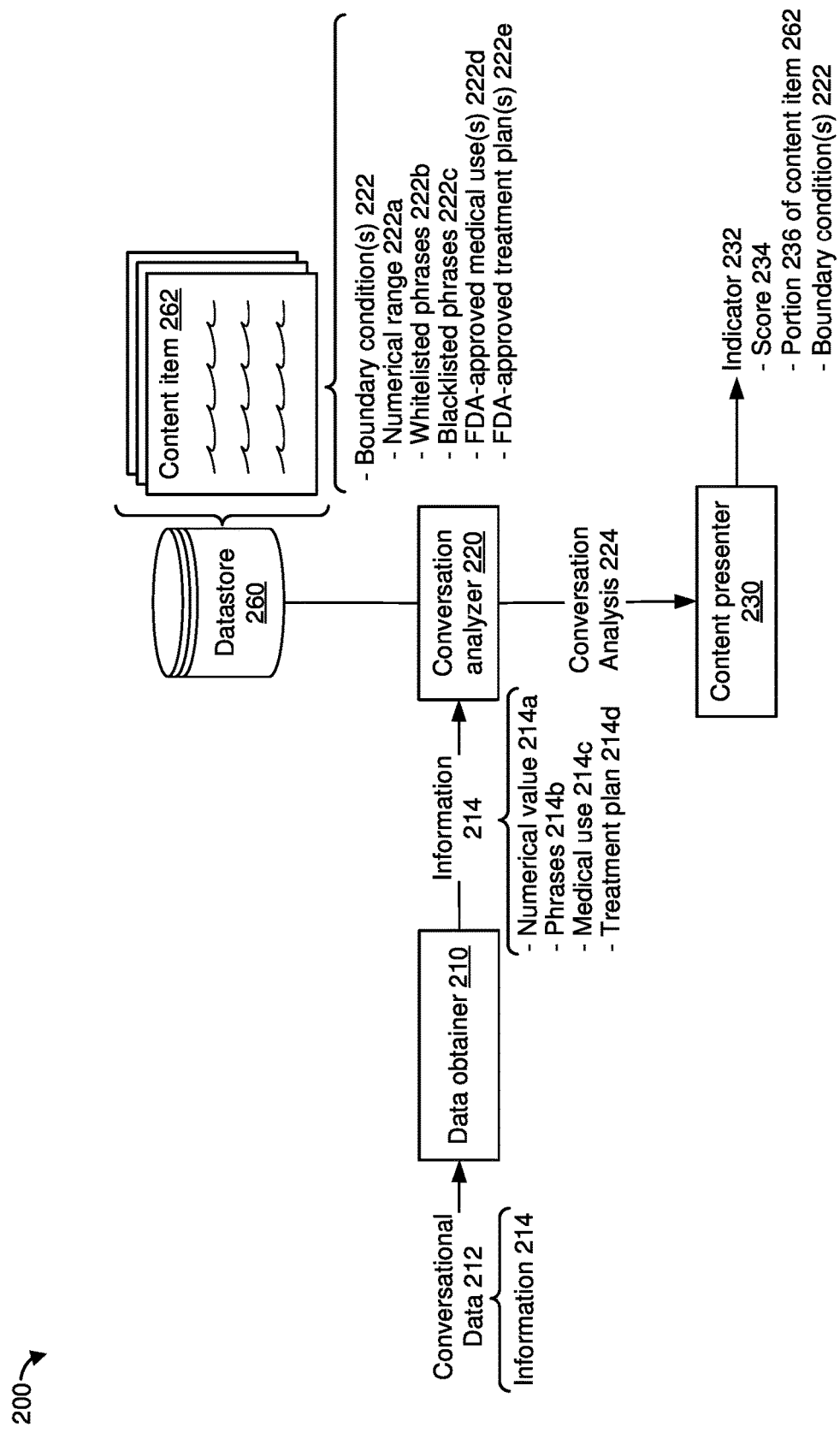
FIG. 2A is a block diagram of a conversational agent in accordance with some implementations.

FIG. 2A is a block diagram of the conversational agent 200 in accordance with some implementations. As described herein, in some implementations, the conversational agent 200 resides at (e.g., is implemented by) the electronic device 20 shown in FIGS. 1A-1F, the electronic device 42 shown in FIGS. 1D-1E, and/or the electronic device 132 shown in FIG. 1G. In various implementations, the conversational agent 200 includes a data obtainer 210, a conversation analyzer 220, a content presenter 230 and a datastore 260.

In various implementations, the datastore 260 stores content items 262 (e.g., the content item(s) 262 shown in FIGS. 1A-1C. In some implementations, the content items 262 include electronic files (e.g., electronic documents). In some implementations, the content items 262 provide information regarding various subjects (e.g., the subject 56 shown in FIGS. 1A-1C). In some implementations, the content items 262 provide information regarding pharmaceutical drugs, medical devices and/or treatment plans for medical conditions. In some implementations, the content items 262 include information that has been approved by the FDA. In some implementations, the content items 262 include FDA-approved labels.

In some implementations, the content items 262 indicate the boundary condition(s) 222 for a subject (e.g., the subject 56 shown in FIGS. 1A-1C). In some implementations, one of the boundary conditions 222 includes a numerical range 222a. For example, in some implementations, the boundary condition 222 for a particular pharmaceutical drug may include a dosage range for that particular pharmaceutical drug (e.g., a dosage quantity range). In some implementations, the boundary conditions 222 include a set of whitelisted phrases 222b (e.g., a set of approved phrases, for example, a set of phrases that have been approved by the FDA). In some implementations, the set of whitelisted phrases 222b correspond to a warning (e.g., a set of medical side effects of a pharmaceutical drug). In some implementations, the boundary conditions 222 include a set of blacklisted phrases 222c (e.g., a set of phrases that have been specifically barred, for example, a set of phrases that the FDA has barred a drug manufacturer from using in connection with their pharmaceutical drug). In some implementations, the boundary conditions 222 include FDA-approved medical use(s) 222d for a pharmaceutical drug or a medical device. In some implementations, the boundary conditions 222 include FDA-approved treatment plan(s) for a medical condition.

In various implementations, the data obtainer 210 obtains conversational data 212 that includes information 214 being conveyed in a conversation. For example, the data obtainer 210 obtains the information 54 shown in FIGS. 1A-1E, the human-curated response 110 shown in FIG. 1F and/or the conversations 140 shown in FIG. 1G. In some implementations, the conversational data 212 includes a transcript of a conversation. In some implementations, the conversational data 212 includes audio corresponding to the conversation (e.g., an audio recording of a previous conversation or live audio for an ongoing conversation). In some implementations, the data obtainer 210 obtains the conversational data 212 via an audio sensor (e.g., a microphone). In various implementations, the data obtainer 210 obtains the conversational data 212 after obtaining consent from a person (e.g., from a user of the conversational agent 200, for example, from the first person 30 shown in FIGS. 1A-1F). In various implementations, the data obtainer 210 provides the information 214 to the conversation analyzer 220.

In various implementations, the conversation analyzer 220 generates a conversation analysis 224 that indicates whether or not the information 214 satisfies the boundary condition(s) 222. In some implementations, the information 214 includes a numerical value 214a. In such implementations, the conversation analyzer 220 determines whether or not the numerical value 214a specified in the information 214 is within the numerical range 222a. If the numerical value 214a specified in the information 214 is within the numerical range 222a, the conversation analysis 224 indicates that the information 214 satisfies the numerical range 222a. If the numerical value 214a specified in the information 214 is outside the numerical range 222a, the conversation analysis 224 indicates that the information 214 breaches (e.g., does not satisfy) the numerical range 222a.

In some implementations, the information 214 includes a set of phrases 214b. In such implementations, the conversation analyzer 220 determines whether or not the set of phrases 214b include one or more of the whitelisted phrases 222b. If the set of phrases 214b specified in the information 214 include one or more of the whitelisted phrases 222b, the conversation analysis 224 indicates that the information 214 satisfies the boundary condition(s) 222. If the set of phrases 214b do not match the whitelisted phrases 222b (e.g., if the set of phrases 214b do not include any of the whitelisted phrases 222b), the conversation analysis 224 indicates that the information 214 breaches the boundary condition(s) 222. For example, if the information 214 does not include a warning related to a pharmaceutical drug or a medical device (e.g., medical side effects of the pharmaceutical drug), the conversation analysis 224 indicates that the information 214 breaches the boundary condition(s) 222.

In some implementations, the conversation analyzer 220 determines whether or not the set of phrases 214b include one or more of the blacklisted phrases 222c (e.g., an unverified medical claim regarding a pharmaceutical drug or medical device). If the set of phrases 214b specified in the information 214 match the blacklisted phrases 222c (e.g., if the set of phrases 214b include the unverified medical claim), the conversation analysis 224 indicates that the information 214 breaches the boundary condition(s) 222. If the set of phrases 214b do not include the blacklisted phrases 222c (e.g., if the set of phrases 214b do not include the unverified medical claim), the conversation analysis 224 indicates that the information 214 satisfies the boundary condition(s) 222. For example, if the information 214 does not include common unverified medical claims regarding a pharmaceutical drug or a medical device, the conversation analysis 224 indicates that the information 214 satisfies the boundary condition(s) 222.

In some implementations, the conversation analyzer 220 determines that the information 214 references a medical use 214c for a pharmaceutical drug or medical device. In such implementations, the conversation analyzer 220 determines whether the medical use 214c matches the FDA-approved medical use(s) 222d for that particular pharmaceutical drug or medical device. If the medical use 214c specified in the information 214 matches the FDA-approved medical use(s) 222d for that particular pharmaceutical drug or medical device, the conversation analysis 224 indicates that the information 214 satisfies the boundary condition(s) 222. If the medical use 214c specified in the information 214 does not match the FDA-approved medical use(s) 222d for that particular pharmaceutical drug or medical device, the conversation analysis 224 indicates that the information 214 breaches the boundary condition(s) 222.

In some implementations, the conversation analyzer 220 determines that the information 214 references a treatment plan 214d for a particular medical condition (e.g., a disease). In some implementations, the conversation analyzer 220 determines whether the treatment plan 214d matches the FDA-approved treatment plan(s) 222e for that particular medical condition. If the treatment plan 214d specified in the information 214 matches the FDA-approved treatment plan(s) 222e for that particular medical condition, the conversation analysis 224 indicates that the information 214 satisfies the boundary condition(s) 222. If the treatment plan 214d specified in the information 214 does not match the FDA-approved treatment plan(s) 222e for that particular medical condition, the conversation analysis 224 indicates that the information 214 breaches the boundary condition(s) 222.

In various implementations, the content presenter 230 displays an indicator 232 based on the conversation analysis 224. For example, the content presenter 230 displays the indicator 60 shown in FIGS. 1B, 1D and 1E, the checkmark 60a and/or the cross 60b shown in FIG. 1C, the indicator 112 shown in FIG. 1F, and/or the scores 154 shown in FIG. 1G. In some implementations, the indicator 232 includes a score 234 (e.g., the scores 154 shown in FIG. 1G). In some implementations, the score 234 indicates what percentage of the information 214 breached the boundary condition(s) 222. In some implementations, the score 234 indicates how often a person that provided the information 214 breaches the boundary condition(s) 222. In some implementations, the indicator 232 includes a portion 236 of one of the content items 262. In some implementations, the portion 236 includes information that the conversational agent 200 utilized to extract the boundary condition(s) 222. In some implementations, the indicator 232 includes the boundary condition(s) 222 that the information 214 breaches.

Figure 2B:
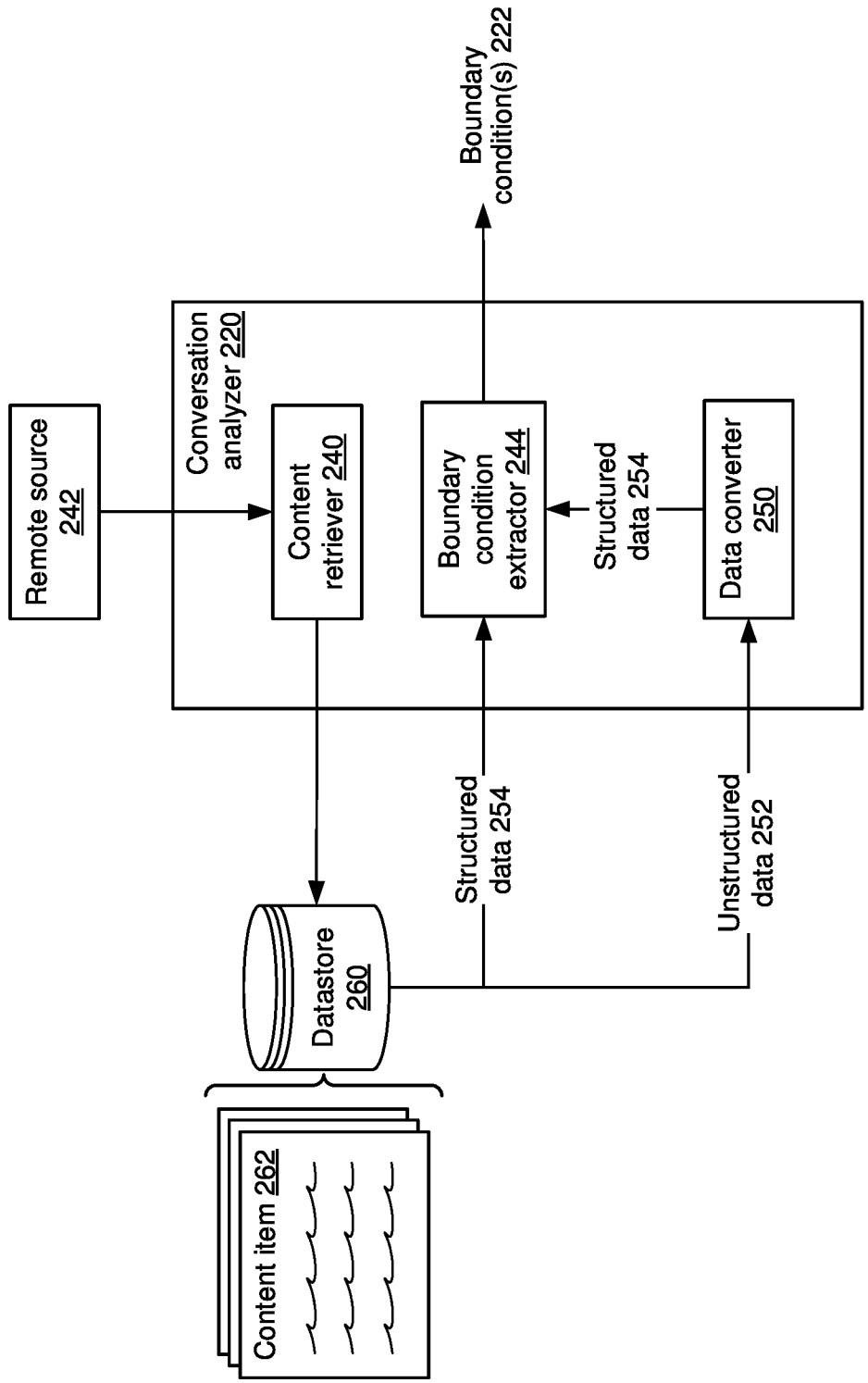
FIG. 2B is a block diagram of a conversation analyzer in accordance with some implementations.

FIG. 2B illustrates an example block diagram of the conversation analyzer 220. In some implementations, the conversation analyzer 220 includes a content retriever 240, a boundary condition extractor 244 and a data converter 250. In various implementations, the content retriever 240 retrieves (e.g., fetches or downloads) the one of more of the content items 262 from a remote source 242. In some implementations, the remote source 242 includes a database that is controlled by a regulatory entity such as the FDA. In some implementations, the remote source 242 includes a database that is controlled by a manufacturing entity such as a pharmaceutical drug manufacturer or a medical device manufacturer. In various implementations, the content retriever 240 stores the retrieved content items 262 in the datastore 260.

In various implementations, the boundary condition extractor 244 extracts the boundary condition(s) 222 from the content items 262 stored in the datastore 260. In some implementations, the content items 262 include structured data 254 that is organized in a defined format that includes labels. In such implementations, the boundary condition extractor 244 extracts the boundary condition(s) 222 by retrieving values associated with the labels. For example, a content item 262 may include 'dosage quantity' as a label. In this example, the boundary condition extractor 244 extracts a value associated with (e.g., displayed adjacent to) the 'dosage quantity' label as one of the boundary condition(s) 222 (e.g., the numerical range 222a shown in FIG. 2A).

In some implementations, the content items 262 include unstructured data 252 that is not organized in a defined format that includes labels. In such implementations, the data converter 250 converts the unstructured data 252 into structured data 254, and provides the structured data 254 to the boundary condition extractor 244. In some implementations, the boundary condition extractor 244 extracts the boundary condition(s) 222 from the structured data 254 that the boundary condition extractor 244 receives from the data converter 250. In some implementations, the data converter 250 converts the unstructured data 252 into the structured data 254 based on metadata associated with the content items 262. In some implementations, the data converter 250 converts the unstructured data 252 into the structured data 254 based on a formatting of the content items 262 (e.g., by identifying headings and/or subheadings in the content items 262).

Figure 3:
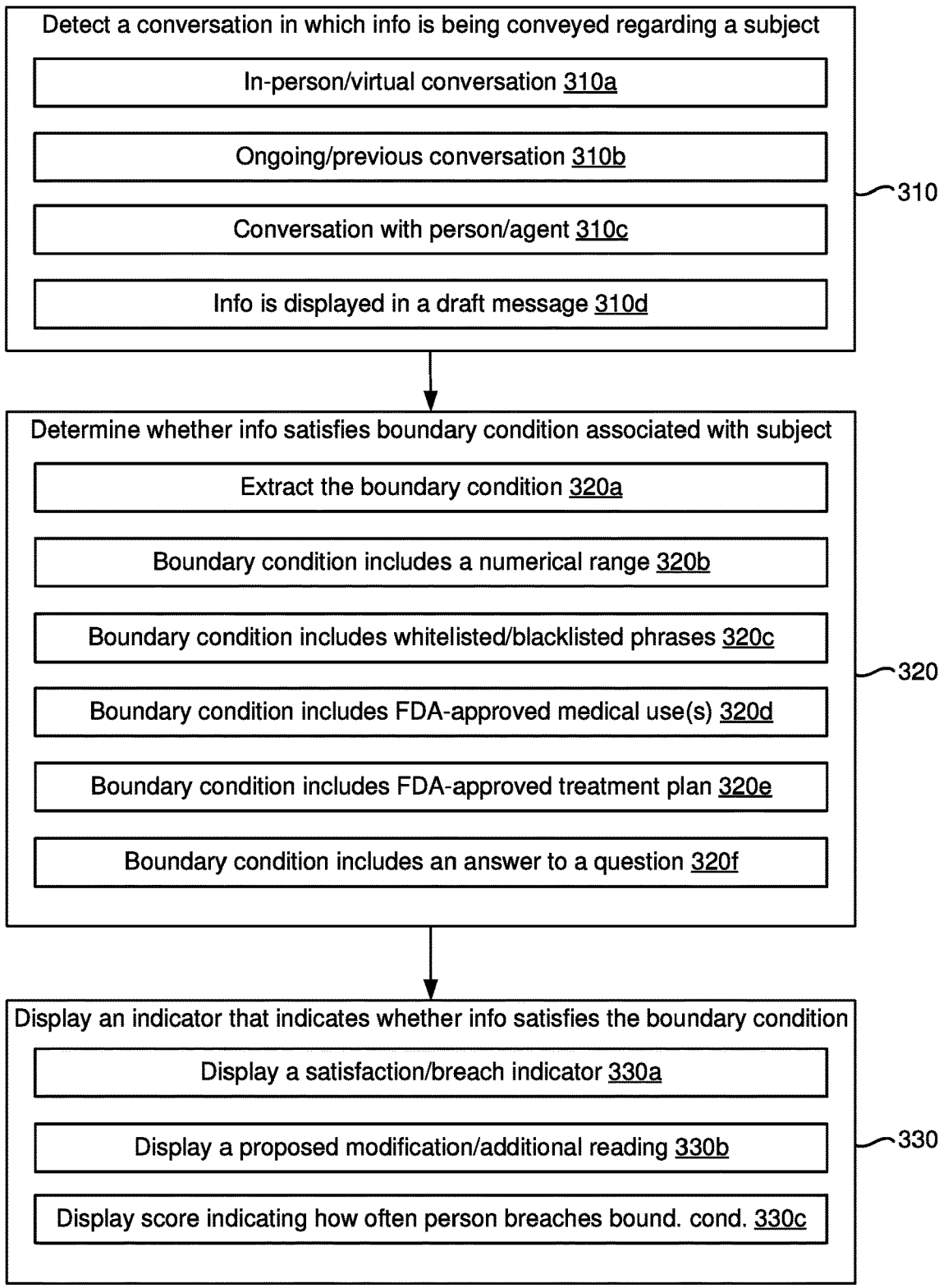
FIG. 3 is a flowchart representation of a method of indicating whether a conversation satisfies a boundary condition in accordance with some implementations.

FIG. 3 is a flowchart representation of a method 300 of indicating whether a conversation regarding a subject satisfies a boundary condition associated with the subject. In various implementations, the method 300 is performed by a device with a display, a processor and a non-transitory memory coupled with the processor and the display (e.g., the electronic device 20 shown in FIGS. 1A-1F, the electronic device 42 shown in FIG. 1E, the electronic device 132 shown in FIG. 1G and/or the conversational agent 200 shown in FIGS. 1-2A). In some implementations, the method 300 is performed by processing logic, including hardware, firmware, software, or a combination thereof. In some implementations, the method 300 is performed by a processor executing code stored in a non-transitory computer-readable medium (e.g., a memory).

As represented by block 310, in some implementations, the method 300 includes detecting a conversation in which a person is conveying information regarding a subject. For example, as shown in FIG. 1A, the electronic device 20 detects that the first person 30 is conveying the information 54 regarding the subject 56. As represented by block 310a, in some implementations, the conversation is an in-person conversation. For example, as shown in FIG. 1A, the first person 30 and the second person 40 are collocated in the operating environment 10, and the conversation 50 is an in-person conversation.

In some implementations, the conversation is a virtual conversation. For example, in some implementations, the conversation is a computer-mediated conversation that occurs via two electronic devices (e.g., the electronic devices 20 and 42 shown in FIG. 1E). In some implementations, the conversation is a video conversation (e.g., a teleconference or a video chat). In some implementations, the conversation is a voice conversation (e.g., a phone call or an audio chat). In some implementations, the conversation is a textual conversation (e.g., a messaging conversation that occurs via an IM application or an email client).

As represented by block 310b, in some implementations, the conversation is ongoing. For example, in some implementations, the conversation includes a current conversation that is currently occurring (e.g., as shown in FIG. 1A or 1E). In some implementations, the conversation occurred previously. For example, in some implementations, the conversation includes a previous conversation that occurred in the past (e.g., the conversations 140 shown in FIG. 1G).

As represented by block 310*c*, in some implementations, the conversation is with another person. In some implementations, the conversation includes a person-to-person conversation (e.g., a human-to-human conversation). For example, as shown in FIGS. 1A-1E, the first person 30 is having the conversation 50 with the second person 40. In some implementations, the conversation is with a virtual agent (e.g., a chatbot). In some implementations, the conversation includes a person-to-machine conversation (e.g., a human-to-machine conversation). For example, as shown in FIG. 1F, the conversation 106 is taking place between the first person 30 and the conversational agent 200.

As represented by block 310*d*, in some implementations, the method 300 includes displaying the information in a message composition region of a graphical user interface. For example, as shown in FIG. 1E, the electronic device 20 displays the information 54 in the message composition region 82 of the messaging GUI 80. In some implementations, the information is about to be conveyed but has not yet been conveyed.

As represented by block 320, in some implementations, the method 300 includes determining whether the information satisfies a boundary condition associated with the subject. In some implementations, the boundary condition is defined by a set of one or more content items related to the subject. For example, as shown in FIG. 2A, the conversation analyzer 220 determines whether or not the information 214 satisfies the boundary condition(s) 222 that are defined by (e.g., extracted from) the content item(s) 262.

As represented by block 320*a*, in some implementations, the method 300 includes extracting the boundary condition from the set of one or more content items. For example, as shown in FIG. 2B, the boundary condition extractor 244 extracts the boundary condition(s) 222 from the content items 262 stored in the datastore 260.

In some implementations, the set of one or more content items include structured data that is organized in a defined format that includes a plurality of labels. In such implementations, extracting the boundary condition includes retrieving a value associated with at least one of the plurality of labels. For example, as shown in FIG. 2B, in some implementations, the content items 262 include structured data 254 that is labeled with labels, and the boundary condition extractor 244 extracts values that are associated with the labels.

In some implementations, the set of one or more content items include unstructured data that is not organized in a defined format that includes a plurality of labels. In such implementations, extracting the boundary condition includes converting the unstructured data into structured data that is organized in the defined format that includes the plurality of labels, and retrieving a value associated with at least one of the plurality of labels. For example, as shown in FIG. 2B, in some implementations, the content items 262 include unstructured data 252, the data converter 250 converts the unstructured data 252 into structured data 252 with labels, and the boundary condition extractor 244 extracts values associated with the labels in the structured data 254.

As represented by block 320*b*, in some implementations, the boundary condition includes a numerical range and the information being conveyed by the person includes a numerical value. In some implementations, determining whether the information satisfies the boundary condition includes determining whether the numerical value being conveyed by the person is within the numerical range indicated by the boundary condition. For example, as shown in FIG. 2A, the information 214 includes the numerical value 214*a*, and the conversation analyzer 220 determines whether the numerical value 214*a* falls within the numerical range 222*a*.

As represented by block 320*c*, in some implementations, the boundary condition includes a set of one or more phrases and the information being conveyed by the person includes a phrase. In some implementations, determining whether the information satisfies the boundary condition includes determining whether the phrase being conveyed by the person is within the set of one or more phrases indicated by the boundary condition. For example, as shown in FIG. 2A, the information 214 includes the set of phrases 214*b*, and the conversation analyzer 220 determines whether the set of phrases 214*b* include the whitelisted phrases 222*b*.

As represented by block 320*d*, in some implementations, the subject is a pharmaceutical drug. In some implementations, the information being conveyed by the person is a medical use for the pharmaceutical drug, dosage information for the pharmaceutical drug or a treatment plan that includes administration of the pharmaceutical drug. In some implementations, the boundary condition includes FDA-approved medical uses for the pharmaceutical drug, FDA-approved dosages for the pharmaceutical drug or FDA-approved treatment plans in which the pharmaceutical drug can be used. In some implementations, the subject is a medical device, the information being conveyed by the person is a medical use for the medical device, and the boundary condition includes FDA-approved medical uses for the medical device. For example, as shown in FIG. 2A, the information 214 indicates a medical use 214*c* for a pharmaceutical drug or a medical device. As described in relation to FIG. 2A, the conversation analyzer 220 determines whether the medical use 214*c* matches the FDA-approved medical use(s) 222*d*.

As represented by block 320*e*, in some implementations, the subject is a medical condition, the information being conveyed by the person is a treatment plan for the medical condition, and the boundary condition includes FDA-approved treatment plans for the medical condition. For example, as shown in FIG. 2A, the information 214 includes a treatment plan 214*d*, and the conversation analyzer 220 determines whether the treatment plan 214 matches the FDA-approved treatment plan(s) 222*e*.

As represented by block 320*f*, in some implementations, the method 300 includes synthesizing, based on a question and answer model, machine-generated questions and corresponding machine-generated answers from the set of one or more content items. For example, as shown in FIG. 1F, the chatbot interface 100 displays a machine-generated message 108 (e.g., a machine-generated question that the conversational agent 200 generated using a question and answer model). In some implementations, the question and answer model includes example questions that are applicable to various subjects.

In some implementations, the information being conveyed by the person is an answer to a question that matches one of the machine-generated questions. In some implementations, determining whether the information satisfies the boundary condition includes determining whether the answer being conveyed by the person matches the corresponding machine-generated answer. For example, as shown in FIG. 1F, the chatbot interface 100 displays a human-curated response 110 (e.g., an answer to the machine-generated question), and the conversational agent 200 determines whether the human-curated response 110 matches a machine-generated answer to the machine-generated question represented by the machine-generated message 108.

As represented by block 330, in some implementations, the method 300 includes displaying an indicator that indicates whether or not the information being conveyed by the person satisfies the boundary condition associated with the subject. In some implementations, displaying the indicator satisfies a resource utilization threshold. For example, in some implementations, displaying the indicator reduces a need for user inputs that correspond to searching through the content items in order to determine whether the information that the person is conveying satisfies the boundary condition. Reducing user inputs tends to enhance a user experience of the device. Reducing user inputs tends to prolong a battery of a battery-operated device thereby improving operability of the device.

As represented by block 330a, in some implementations, the indicator includes a satisfaction indicator that indicates that the information satisfies the boundary condition associated with the subject. For example, as shown in FIG. 1C, the electronic device 20 displays the checkmark 60a adjacent to the first portion Ma of the information 54 in order to indicate that the first portion 54a of the information 54 satisfies the boundary condition(s) 222.

In some implementations, the indicator includes a breach indicator that indicates that the information breaches the boundary condition associated with the subject. For example, as shown in FIG. 1C, the electronic device 20 displays a cross 60b adjacent to the second portion 54b of the information 54 in order to indicate that the second portion 54b of the information breaches the boundary condition(s) 222.

In some implementations, the indicator includes a satisfaction indicator that indicates that a first portion of the information satisfies the boundary condition and a breach indicator that indicates that a second portion of the information breaches the boundary condition. For example, as shown in FIG. 1C, the electronic device 20 displays the checkmark 60a to indicate that the first portion Ma of the information 54 satisfies the boundary condition(s) 222, and the cross 60b to indicate that the second portion 54b of the information 54 breaches the boundary condition(s) 222.

As represented by block 330b, in some implementations, the indicator includes a proposed modification to the information in order to satisfy the boundary condition associated with the subject. In some implementations, the method 300 includes displaying a portion of the set of one or more content items in response to the information breaching the boundary condition. In some implementations, the boundary condition is derived from the portion. For example, if a medical representative is conveying the wrong dosage information for a pharmaceutical drug, then the electronic device 20 displays a portion of the FDA-approved label that includes the correct dosage information for the pharmaceutical drug.

As represented by block 330c, in some implementations, the indicator includes a score that indicates how often the person provides information that satisfies or breaches the boundary condition. For example, as shown in FIG. 1G, the electronic device 132 displays the scores 154 for different persons.

Figure 4:
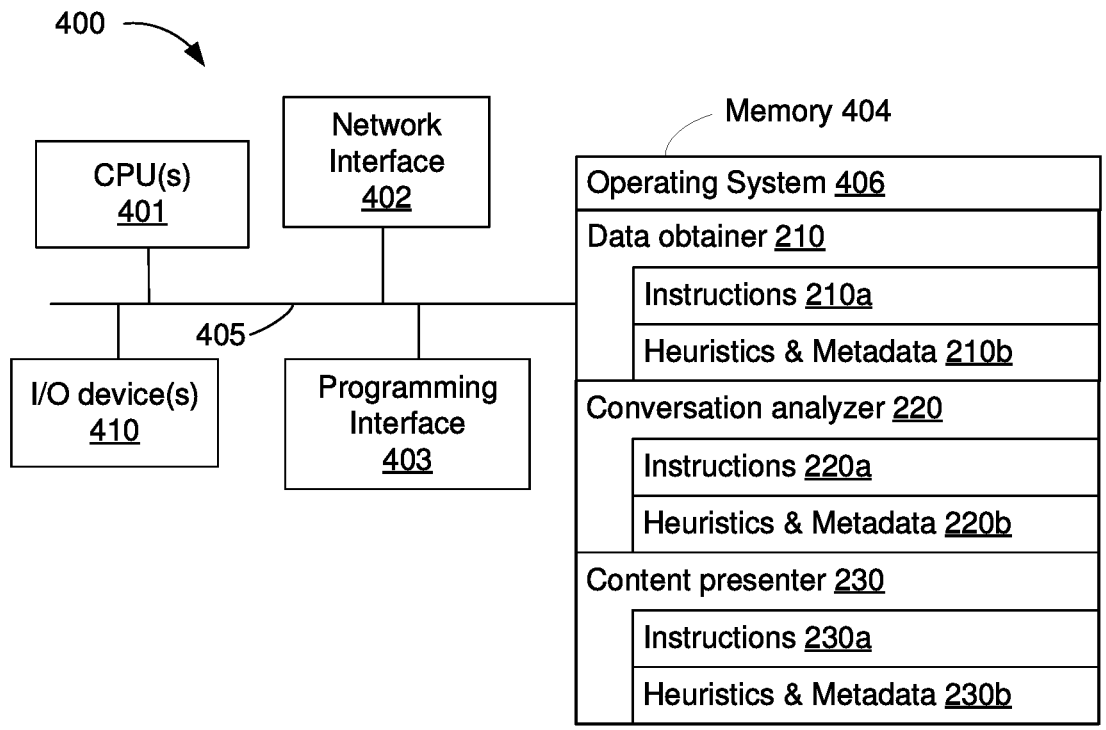
FIG. 4 is a block diagram of a device that implements a conversational agent in accordance with some implementations.

FIG. 4 is a block diagram of a device 400 that indicates whether a conversation satisfies a boundary condition in accordance with some implementations. In some implementations, the device 400 implements the electronic device 20 shown in FIGS. 1A-1F, the electronic device 42 shown in FIG. 1E, the electronic device 132 shown in FIG. 1G and/or the conversational agent 200 shown in FIGS. 1-2A. While certain specific features are illustrated, those of ordinary skill in the art will appreciate from the present disclosure that various other features have not been illustrated for the sake of brevity, and so as not to obscure more pertinent aspects of the implementations disclosed herein. To that end, as a non-limiting example, in some implementations the device 400 includes one or more processing units (CPUs) 401, a network interface 402, a programming interface 403, a memory 404, one or more input/output (I/O) devices 410, and one or more communication buses 405 for interconnecting these and various other components.

In some implementations, the network interface 402 is provided to, among other uses, establish and maintain a metadata tunnel between a cloud hosted network management system and at least one private network including one or more compliant devices. In some implementations, the one or more communication buses 405 include circuitry that interconnects and controls communications between system components. The memory 404 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. The memory 404 optionally includes one or more storage devices remotely located from the one or more CPUs 401. The memory 404 comprises a non-transitory computer readable storage medium.

In some implementations, the memory 404 or the non-transitory computer readable storage medium of the memory 404 stores the following programs, modules and data structures, or a subset thereof including an optional operating system 406, the data obtainer 210, the conversation analyzer 220, and the content presenter 230. In various implementations, the device 400 performs the method 300 shown in FIG. 3.

In some implementations, the data obtainer 210 detects a conversation in which information is being conveyed regarding a subject. In some implementations, the data obtainer 210 performs the operation(s) represented by block 310 in FIG. 3. To that end, the data obtainer 210 includes instructions 210a, and heuristics and metadata 210b.

In some implementations, the conversation analyzer 220 determines whether the information being conveyed in the conversation satisfies a boundary condition associated with the subject. In some implementations, the conversation analyzer 220 performs the operations(s) represented by block 320 shown in FIG. 3. To that end, the conversation analyzer 220 includes instructions 220a, and heuristics and metadata 220b.

In some implementations, the content presenter 230 displays an indicator that indicates whether or not the information satisfies the boundary condition associated with the subject. In some implementations, the content presenter 230 performs the operation(s) represented by block 330 shown in FIG. 3. To that end, the content presenter 230 includes instructions 230a, and heuristics and metadata 230b.

In some implementations, the one or more I/O devices 410 include an audio sensor (e.g., a microphone) for capturing audio corresponding to a conversation. In some implementations, the one or more I/O devices 410 include an image sensor (e.g., a camera). In some implementations, the one or more I/O devices 410 include a display (e.g., the display 22 shown in FIG. 1B) for displaying the indicator.

While various aspects of implementations within the scope of the appended claims are described above, it should be apparent that the various features of implementations described above may be embodied in a wide variety of forms and that any specific structure and/or function described above is merely illustrative. Based on the present disclosure one skilled in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

It will also be understood that, although the terms "first", "second", etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting", that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

What is claimed is:

1. A method comprising:
    at a first device including, a microphone, a display, a processor, a battery and a non-transitory memory:
        displaying, on the display, a messaging graphical user interface (GUI) to enable a messaging conversation between a medical representative using the first device and a healthcare provider using a second device, wherein the messaging GUI includes:
            a message composition region for composing a message from the medical representative to the healthcare provider,
            a send affordance for sending the message to the healthcare provider, and
            one or more previous messages that have been sent or received by the first device;
        detecting, within the message composition region of the messaging GUI, a value that characterizes a pharmacological characteristic of a pharmaceutical drug or a medical device that is regulated by the Food and Drug Administration (FDA);
        obtaining, from a datastore, an FDA-approved value that characterizes the pharmacological characteristic of the pharmaceutical drug or the medical device, wherein the FDA-approved value is extracted from an FDA-approved label for the pharmaceutical drug or the medical device;
        prior to sending the message to the healthcare provider, determining whether the value being conveyed in the message satisfies the FDA-approved value; and
        in response to determining that the value being conveyed in the message does not satisfy the FDA-approved value, prior to sending the message to the healthcare provider:
            displaying, on the display, a breach indicator indicating that the value being conveyed in the message breaches the FDA-approved value;
            displaying, on the display, the FDA-approved value;
            displaying, on the display, a portion of the FDA-approved label that specifies the FDA-approved value; and
            providing an option to modify the value before the message is sent to the healthcare provider.

2. The method of claim 1, further comprising extracting the FDA-approved value from the FDA-approved label.

3. The method of claim 2, wherein the FDA-approved label includes structured data that is organized in a defined format that includes a plurality of labels, and wherein extracting the FDA-approved value includes retrieving a value associated with at least one of the plurality of labels.

4. The method of claim 2, wherein the FDA-approved label includes unstructured data that is not organized in a defined format that includes a plurality of labels; and
    wherein extracting the FDA-approved value comprises:
        converting the unstructured data into structured data that is organized in the defined format that includes the plurality of labels; and
        retrieving a value associated with at least one of the plurality of labels.

5. The method of claim 1, wherein the FDA-approved value includes a numerical range and the value being conveyed in the message includes a numerical value; and
    wherein determining whether the value satisfies the FDA-approved value includes determining whether the numerical value being conveyed in the message is within the numerical range indicated by the FDA-approved value.

6. The method of claim 1, wherein the FDA-approved value includes a set of one or more phrases and the value being conveyed in the message includes a phrase; and
    wherein determining whether the value satisfies the FDA-approved value includes determining whether the phrase being conveyed in the message is within the set of one or more phrases indicated by the FDA-approved value.

7. The method of claim 1, wherein the value being conveyed in the message is a medical use for the pharmaceutical drug, dosage information for the pharmaceutical drug or a treatment plan that includes administration of the pharmaceutical drug; and wherein the FDA-approved value includes FDA-approved medical uses for the pharmaceutical drug, FDA-approved dosages for the pharmaceutical drug or FDA-approved treatment plans in which the pharmaceutical drug can be used.

8. The method of claim 1, wherein the value being conveyed in the message is a medical use for the medical device; and
wherein the FDA-approved value includes FDA-approved medical uses for the medical device.

9. The method of claim 1, wherein the value being conveyed in the message is a treatment plan that utilizes the pharmaceutical drug or the medical device to treat a medical condition; and
wherein the FDA-approved value includes FDA-approved treatment plans for the medical condition.

10. The method of claim 1, further comprising:
synthesizing, based on a question and answer model, machine-generated questions and corresponding machine-generated answers from the FDA-approved label.

11. The method of claim 10, wherein the value being conveyed in the message is an answer to a question that matches one of the machine-generated questions; and
wherein determining whether the value satisfies the FDA-approved value includes determining whether the answer being conveyed by the person matches the corresponding machine-generated answer.

12. The method of claim 1, wherein the FDA-approved label includes a set of one or more documents.

13. The method of claim 1, further comprising:
in response to determining that the value being conveyed in the message satisfies the FDA-approved value, displaying, on the display, a satisfaction indicator that indicates that the value satisfies the FDA-approved value.

14. The method of claim 1, further comprising:
detecting that the message is conveying a second value that characterizes a second pharmacological characteristic of the pharmaceutical drug or the medical device;
in response to the second value satisfying a second FDA-approved value that characterizes the second pharmacological characteristic of the pharmaceutical drug or the medical device:
displaying a satisfaction indicator that indicates that second value satisfies the second FDA-approved value in addition to displaying the breach indicator indicating that the value does not satisfy the FDA-approved value.

15. The method of claim 1, wherein the breach indicator includes a proposed modification to the value in order to satisfy the FDA-approved value.

16. The method of claim 1, further comprising:
displaying a score that indicates how often the person provides information that satisfies or breaches FDA-approved values in the FDA-approved label.

17. A non-transitory memory storing one or more programs, which, when executed by one or more processors of a first device, cause the first device to:
display, on a display, a messaging graphical user interface (GUI) to enable a messaging conversation between a medical representative using the first device and a healthcare provider using a second device, wherein the messaging GUI includes:
a message composition region for composing a message from the medical representative to the healthcare provider,
a send affordance for sending the message to the healthcare provider, and
one or more previous messages that have been sent or received by the first device;
detect, within the message composition region of the messaging GUI, a value that characterizes a pharmacological characteristic of a pharmaceutical drug or a medical device that is regulated by the Food and Drug Administration (FDA);
obtain, from a datastore, an FDA-approved value that characterizes the pharmacological characteristic of the pharmaceutical drug or the medical device, wherein the FDA-approved value is extracted from an FDA-approved label for the pharmaceutical drug or the medical device;
prior to sending the message to the healthcare provider, determine whether the value being conveyed in the message satisfies the FDA-approved value; and
in response to determining that the value being conveyed in the message does not satisfy the FDA-approved value, prior to sending the message to the healthcare provider:
display, on the display, a breach indicator indicating that the value being conveyed in the message breaches the FDA-approved value;
display, on the display, the FDA-approved value;
display, on the display, a portion of the FDA-approved label that specifies the FDA-approved value; and
provide an option to modify the value before the message is sent to the healthcare provider.

18. A first device comprising:
one or more processors;
a non-transitory memory;
a microphone;
one or more displays;
a battery; and
one or more programs stored in the non-transitory memory, which, when executed by the one or more processors, cause the first device to:
display, on the one or more displays, a messaging graphical user interface (GUI) to enable a messaging conversation between a medical representative using the first device and a healthcare provider using a second device, wherein the messaging GUI includes:
a message composition region for composing a message from the medical representative to the healthcare provider,
a send affordance for sending the message to the healthcare provider, and
one or more previous messages that have been sent or received by the first device;
detect, within the message composition region of the messaging GUI, a value that characterizes a pharmacological characteristic of a pharmaceutical drug or a medical device that is regulated by the Food and Drug Administration (FDA);
obtain, from a datastore, an FDA-approved value that characterizes the pharmacological characteristic of the pharmaceutical drug or the medical device, wherein the FDA-approved value is extracted from an FDA-approved label for the pharmaceutical drug or the medical device;
prior to sending the message to the healthcare provider, determine whether the value being conveyed in the message satisfies the FDA-approved value; and in response to determining that the value being conveyed in the message does not satisfy the FDA-approved value, prior to sending the message to the healthcare provider:
- display, on the one or more displays, a breach indicator indicating that the value being conveyed in the message breaches the FDA-approved value;
- display, on the one or more displays, the FDA-approved value;
- display, on the one or more displays, a portion of the FDA-approved label that specifies the FDA-approved value; and
- provide an option to modify the value before the message is sent to the healthcare provider.

* * * * *